United States Patent [19]
Michalski et al.

[11] Patent Number: 5,457,181
[45] Date of Patent: Oct. 10, 1995

[54] PREPARATION OF A HIGH-PURITY HUMAN FACTOR IX CONCENTRATE AND OTHER PLASMATIC PROTEINS AND THEIR THERAPEUTIC USE

[75] Inventors: Catherine Michalski, Lille; Thierry Burnouf, Wavrin, both of France

[73] Assignee: Centre Regional de Transfusion Sanguine de Lille, Lille, France

[21] Appl. No.: 683,109

[22] Filed: Apr. 11, 1991

Related U.S. Application Data

[63] Continuation of Ser. No. 260,017, Oct. 20, 1988, abandoned.

[30] Foreign Application Priority Data

Oct. 23, 1987 [FR] France .................................. 87 14665
May 25, 1988 [FR] France .................................. 88 06923

[51] Int. Cl.$^6$ .............................. C07K 1/16; C07K 1/18; C07K 1/22
[52] U.S. Cl. .......................... 530/381; 530/380; 530/384; 530/413; 530/416
[58] Field of Search ..................... 530/380, 381, 530/384, 413, 416; 424/101

[56] References Cited

U.S. PATENT DOCUMENTS

| | | | |
|---|---|---|---|
| 4,081,431 | 3/1978 | Stephan et al. | 530/383 |
| 4,374,763 | 2/1983 | Takagi et al. | 530/387 |
| 4,397,841 | 8/1983 | Johnson et al. | 424/101 |
| 4,440,679 | 4/1984 | Fernandes et al. | 530/381 |
| 4,447,416 | 5/1984 | Menache-Aronson | 514/2 |
| 4,540,573 | 9/1985 | Neurath et al. | 530/380 |
| 4,777,043 | 10/1988 | Bennett et al. | 424/94.64 |

FOREIGN PATENT DOCUMENTS

| | | |
|---|---|---|
| 0041174 | 12/1981 | European Pat. Off. . |
| 0137428 | 4/1985 | European Pat. Off. . |
| 0229026 | 7/1987 | European Pat. Off. . |
| 2080312 | 2/1982 | United Kingdom . |

OTHER PUBLICATIONS

Hashimoto et al (1985), Journal of Biochemistry, vol. 97, pp. 1347–1355.
Bajaj et al (1982), Chemical Abstracts, vol. 96, p. 361, No. 100322g.
Chemical Abstracts, vol. 108, p. 345, No. 164242e (1988).
Journal of Chromatography, vol. 363 (1986), pp. 101–103.
Chemical Abstracts, vol. 107, No. 23, Dec. 7, 1987, p. 259, No. 213990n.
Fujikawa et al. (1973) Biochemistry 12, 4938–4945.
Pharmacia Fine Chemicals AB Publications (1980), Ion Exchange Chromatography: Principles and Methods, Uppsala.

*Primary Examiner*—Robert A. Wax
*Assistant Examiner*—Kawai Lau
*Attorney, Agent, or Firm*—Birch, Stewart, Kolasch & Birch

[57] ABSTRACT

The present invention relates to a method for preparing a high purity Factor IX concentrate. The starting material for the process is the supernatant fraction of a cryoprecipitated human plasma. A pre-purification step is performed by DEAE-Sephadex chromatography. The resulting Factor IX fraction has a specific activity of at least 0.5 IU/mg protein. The purification method of the invention comprises two successive chromatography separations. First, ion-exchange chromatography on DEAE-sepharose is conducted so that the Factor IX is eluted when the ionic force of the buffer is increased to 0.34–0.38M sodium chloride. Then, affinity chromatography is conducted on heparin-sepharose. The elution buffer is a citrate buffer at a pH of 7.4 adjusted with 0.45M sodium chloride and supplemented with arginine as a stabilizer for Factor IX activity. Lysine is added as a stabilizer before freeze-drying of the purified Factor IX.

15 Claims, No Drawings

PREPARATION OF A HIGH-PURITY HUMAN FACTOR IX CONCENTRATE AND OTHER PLASMATIC PROTEINS AND THEIR THERAPEUTIC USE

This application is a continuation of application Ser. No. 07/260,017 filed on Oct. 20, 1988, now abandoned.

FIELD OF THE INVENTION

The present invention relates to obtaining a high-purity Factor IX concentrate by means of ion exchange chromatography and affinity chromatography techniques using as a starting material a fraction of any human plasma containing Factor IX. The method of the present invention also makes it possible to obtain fractions enriched with alpha-antitrypsin, protein C and protein S, proconvertin or Factor VII, prothrombin or Factor II and Stuart factor or Factor X. The method also makes it possible to recover albumin, antithrombin III and immunoglobulins.

BACKGROUND OF THE INVENTION

Making available Factor VII concentrates and Factor IX concentrates which are free from other proteins with clotting activities would be extremely beneficial for patients deficient in both Factor VII and Factor IX (B hemophiliacs). In fact, these two categories of illness are currently treated by using concentrates of plasmatic proteins of a prothrombin complex (also known as PPSB) containing four clotting proteins, namely Factors II, VII, IX and X. Subjected during their haemorrhage episodes to treatment by PPSB, patients deficient in Factor VII and those deficient in Factor IX receive large doses of other clotting factors (Factors II and X) whereas, prior to treatment, they have normal levels. This excess of clotting proteins may induce a risk of thrombosis. This danger is more likely with those patients deficient in Factor VII, as in vivo this protein has a relatively short half-life (7 to 9 hours) which, in order to reestablish normal physiological levels, involves injecting massive doses of PPSB and thus of Factors II, IX and X. This phenomenon is amplified by the fact that PPSB is usually poor in Factor VII (10 to 18 IU/ml as compared with 30 to 45 IU/ml of Factor X, for example). Treatments with total plasma have been proposed, but these induce well-known risks of vital contamination as the therapeutic plasma is usually not inactivated with regard to pathogenic viruses. These treatments also require the same massive and repeated injections as with PPSB and results in a build up of accessory plasma-derived proteins.

Although there are certain publications demonstrating the usefulness of ion exchange (DEAE) chromatography and affinity chromatography (heparin-Sepharose) (Andersson et al., Thrombosis Research; 7, 451–459, 1975), there are few specific therapeutic Factor VII and Factor IX concentrates. There currently exists a Factor VII concentrate, but this derivative contains antigens of Factors IX, II and X, protein C and large doses of heparin. A method for preparing a high-purity Factor IX concentrate has been published (Menaché et al., Blood, 64, 1220–1227, 1984); however this method uses two chromatographic adsorption steps. The first step is batch processing in the presence of DEAE-Sephadex, and the second step is a passage through a column of dextran sulfate gel. This technique consists of purifying PPSB (DEAE-Sephadex) and then isolating Factor IX by virtue of its affinity for dextran sulfate. However, this method does not offer all the advantages of industrial column chromatography due to the batch adsorption step (a method that can only be slightly automated and which is poorly reproducible) and impairs the optimized recovery of other potentially useful plasmatic fractions. Finally, it does not favor the simultaneous recovery of proconvertin.

SUMMARY OF THE INVENTION

The Applicant has now discovered a method using conventional chromatographic techniques, that could be used on any fraction of human plasma containing Factor IX so as to provide, after the fraction has been suitably treated, a high-purity Factor IX, having having a specific activity greater than 120 IU/mg and mainly free from Factors II, VII and X.

The invention thus relates to a method for preparing high-purity Factor IX, wherein a fraction of human plasma undergoes a prepurification step so as to eliminate lipidic and proteinaceous contaminants and then subject this prepurified fraction to chromatographic treatment, combining among others anion exchange chromatography and affinity chromatography.

DETAILED DESCRIPTION OF THE INVENTION

As indicated above, the method of the invention can be applied to any plasmatic fraction containing Factor IX and in particular to fractions which also contain Factors II, X and VII, as well as proteins S and C, which may then also be separated by means of said method.

Amongst the possible treatments to which the plasmatic fraction could be subjected, one could cite:
- adsorption on soft or rigid ion exchange resins,
- treatment with tricalcium phosphate,
- treatment with barium sulphate or barium chloride,
- precipitation with ammonium sulphate,
- adsorption on aluminum gel.

These various treatments adsorb Factor IX, as well as Factors II, VII and X possibly present which are desorbed before undergoing the subsequent chromatographic steps.

The prepurification treatment is designed to obtain a fraction in which the specific activity of Factor IX is greater than or equal to 0.5 IU/mg. Generally speaking, a specific actifity of about 1 IU/mg enables the method to be used satisfactorily and allows Factor IX having the desired purity to be obtained.

The eluate of this prepurification column contains albumin, immunoglobins, antithrombin III and alpha-antitrypsin; these different substances can be subsequently purified and concentrated.

The subsequent chromatographic steps are preferably carried out by using ion exchange chromatography, for example on DEAE Sepharose, this chromatography being possibly carried out in the presence of heparin, followed by affinity chromatography, especially on immobilized heparin.

According to another aspect of the invention, prepurification may be replaced by a step of diluting-filtrating the cryoprecipitate supernatent with osmosed water so as to reduce its ionic force and allow for adsorption of selected proteins on the chromatographic gel. Advantageously, heparin is added to a final dose of 1 IU/ml.

According to this particular aspect of the invention, the α antitrypsin shall be retained by the first anion exchange chromatography column; it could be desorbed by a buffer containing between 0.13 and 0.17M of NaCl, more particularly adjusted to 0.16M of NaCl and at a slightly acid pH.

Of course, it is possible to provide at any stage of the method a vital inactivation treatment by means of a technique well-known to anyone skilled in the art.

However, particularly satisfactory results have been obtained by subjecting the prepurified plasma fraction to a solvent-detergent treatment, such as the one described in the European patent application No. 0 131 740.

The process according to the invention includes chromatography on an anion exchanger resin and more particularly on a DEAE-Sepharose gel; by means of elution with a buffer of increasing ionic force, three fractions are recovered respectively enriched in proconvertin (Factor VII), proteins C and S and an alpha-inter-trypsin inhibitor and finally with Factor IX, II and X.

The fraction rich in proconvertin is desorbed by a buffer containing a NaCl concentration of 0.18 to 0.20M and preferably 0.19M and at a slightly acid pH. As soon as it elutes, it is advisable to add to it a dose of 1 IU/ml (final concentration) of human antithrombin III. The fraction is then concentrated and at this stage the heparin concentration is adjusted between 5 and 10 IU/ml and preferably to 5 IU/ml.

This method makes it possible to obtain, with a yield of about 45%, a proconvertin with a specific activity of at least 0.7 IU/mg of protein.

The recovery of other plasmatic fractions adsorbed on the anion exchanger resin occurs by gradually increasing the ionic force.

Thus, a fraction containing proteins C and S but free from the other clotting factors (II, VII, IX, X) is preferably eluted by increasing the saline concentration of the chromatographic buffer. The salt concentration, preferably sodium chloride, shall be between 0.26 and 0.30M and is advantageously adjusted to 0.28M and at a slightly acid pH.

The fraction rich in Factors IX, II and X is eluted by a new increase of the saline concentration of the chromatographic buffer, the latter being brought between 0.34 and 0.38M of sodium chloride and preferably 0.36M, the pH being adjusted to 8.0.

After this chromatography on the anion exchange rein, the method according to the invention includes a new purification step by affinity chromatography allowing in particular for the separation of Factors II and X. This affinity chromatography is preferably carried out on immobilized heparin and, preferably on heparin-sepharose in a citrate buffer.

This chromatography makes it possible to separate a filtrate containing Factor II which may subsequently be collected in order to prepare thrombin.

By increasing the saline concentration in the citrate buffer and, more precisely, by adjusting the quantity of sodium chloride in the 0.23–0.27M range and more favorably 0.25M, one elutes a fraction rich in Factor X and possibly containing proteins C and F inhibitors and alpha-intertrypsin inhibitor.

Finally, by raising the NaCl concentration to a dose of about 0.43–0.47M or more and preferably 0.45M, a fraction rich in Factor X is eluted. This fraction is then concentrated by ultrafiltration and freeze-dried.

By starting, for example, with a cryoprecipitate supernatent containing Facteur IX in a quantity corresponding to a specific activity of 0,014 IU/mg, the use of this method makes it possible to obtain a high-purity Factor IX, of about 120 IU/mg of protein.

In order to favor the stability of Factor IX, it is possible to provide one or more stabilizers which protect it from degradation and avoid loss of coagulant activity. Preferably, these stabilizers are added to the elution buffer.

Amongst the various substances evaluated, arginine appeared to be particularly effective for stabilizing Factor IX. Preferably, 1 g/l, for example between 1 and 5 g/l, is used as a minimum dose.

Moreover, it may also be advisable to protect Factor IX, especially relating to its freeze-drying, by adding another stabilizer as soon as it elutes from the chromatographic column. In this case, lysine is preferably used at a concentration of at least 0.5 g/L, for example between 0.5 and 2 g/l.

The product thus obtained may be advantageously used in therapeutics, especially for the treatment of hemophilia B. As compared with equivalent substances already used, this product has the advantage of being free from other coagulant factors, plasmatic proteins and lipidic contaminants.

The following example illustrates the invention without, however, limiting its scope.

EXAMPLE

As a starting material, a cryoprecipitate supernatent is used which is obtained by thawing and centrifugating at 0°–3° C. a frozen fresh plasma. This material contains Factor IX (specific activity 0.014 IU/mg).

1. Prepurification

A supernatent batch is treated with DEAE-Sephadex A 50 resin in the presence of physiological serum. After washing with 0.20M of sodium chloride in a 0.01M citrate buffer at a pH of 7.0, the elution is performed with 2M of sodium chloride in a 0.01M citrate buffer at a pH of 7.0. The salt is then eliminated by ultrafiltration.

The specific activity of Factor IX in this prepurified fraction is in the range of 1 IU/mg.

The eluate of this prepurification column contains among other proteins, albumin, immunuglobulins, antithrombin III, alpha-antitrypsin and transfertin, which may be subsequently collected, prufied and concentrated.

Alternatively, it is possible to replace this prepurification on Sephadex by a step of diluting and filtrating the cryoprecipitate supernatent with osmosed water (⅓ dilution). The heparin is added to a final concentration of 1 IU/ml after filtration. In this case, albumin, immunoglobulins and antithrombin III shall be recovered in the filtrate of the next column and the alpha-antitrypsin shall be adsorbed on the column. It could also be eluted by a low ionic force buffer containing, for example, 0.16M of NaCl at a pH of 6.0; it could then be further purified by chromatography on Sephacryl S-200 (Pharmacia), according to a protocol which has been described in the European Patent Application 88.400235.3.

It should be noted that this dilution/filtration step will not obtain at the end of the process a Factor IX as purified as it would be when a prepurification step on Sephadex is used. With only 30% yield, a Factor IX with specific activity of 5 to 10 IU/mg of protein shall be obtained.

2. Anion exchange chromatography

The prepurified fraction, desorbed from the resin described above and containing Factor IX and Factors II, VII and X, with 1 IU/ml of heparin (final concentration) possibly added, is injected onto a DEAE-Sepharose CL 6B column (Pharmacia) filled to equilibrium with a phosphate buffer at pH 6.0.

In order to insure vital inactivation, prior to injection on the column, it is possible to carry out a solvent-detergent type treatment by using 0.3 % of tri-n-butyl phosphate and 1% Tween 80 (Merck), said treatment being performed at 24° C. for 6 hours.

The different molecules are desorbed from the column by means of elution with an increasing ionic force buffer.

Recovery of the Fraction Rich in Factor VII (proconvertin)

By elution with a 6 mM phosphate buffer in the presence of sodium citrate 5 mM mixed with sodium chloride 0.19M, a fraction rich in Factor VII is collected. To this, antithrombin III is added at a final concentration of 1 IU/ml. After ultrafiltration in order to adjust the protein concentration to about 30 g/l, the heparin concentration is adjusted to 5 IU/ml and the concentrate is distributed at a rate of 20 ml per bottle and is freeze-dried.

Analysis of the concentrate thus obtained reveals that the proconvertin is present here with an activity of about 25 IU/ml for a specific activity usually in the range of 1.0 to 2.0 IU/mg of protein. One also confirms the absence of clotting Factors II, IX and X, which would contribute in increasing the thrombogenicity of the product, and the absence of protein C. The weak thrombogenic power of the product is further corroborated by "in vitro" tests (NAPTT, TGT 50) and "in vivo" (effective dose 50 (ED50) on rabbits higher than 500 IU/kg as compared with about 30 to 60 IU/kg with the PPSB.

The characteristics of the product establish that it provides significant improvements to anti-haemorrhage treatments for patients having a proconvertin deficit.

Recovery of the Protein C and Protein S Fraction

The fraction in question is desorbed from the DEAE-Sepharose column by passage of the phosphate buffer in the presence of 5 mM of sodium citrate at a pH of 6.0 containing 0.28M of sodium chloride.

The eluate has the following content:

| | |
|---|---|
| Protein C | 5 IU/ml |
| Protein S | 5 IU/ml |

It is free from coagulation Factors II, VII, IX and X.

Elution of the Fraction Containing Factors II, IX and X

This fraction is eluted by passage of the 5 mM citrate-phosphate buffer adjusted to a pH of 8.0 and containing 0.36M of sodium chloride.

Factor IX is present in the eluate in a quantity corresponding to a specific activity of about 3 IU/mg. It has been ensured that this fraction did not contain any Factor VII:C.

3. Affinity chromatography on immobilized heparin and preparation of the Factor IX concentrate.

The last fraction eluted from the previous column contains a mixture of Factors II, IX and X; it is dialyzed to adjust the ionic strength and stabilizer is added at a concentration of 3 g/l; it is then injected onto a column containing a heparin-sepharose chromatographic gel balanced with the 20 mM citrate buffer, pH 7.4.

A filtrate containing Factor II is collected.

The gel is then subjected to an elution by the citrate buffer enriched with 0.25M NaCl and a Factor X-enriched fraction is collected.

By further elution with buffer containing 0.45M sodium chloride, to which 3.5 g/l of arginine is added as a statilizer, the Factor IX concentrate is collected.

As soon as it elutes one adds, 1 g/l of lysine as a stabilizer, and optionally heparin at a final concentration of 5 IU/ml. The product is then concentrated by ultrafiltration, sterilized by filtration and freeze-dried.

The average biochemical characteristics of the product are indicated hereunder:

| | |
|---|---|
| Proteins (g/l | 0.19 ± 0.03 |
| Factor IX:C (IU/ml) | 25 ± 3 |
| Factor IX specific activity (IU/mg) | 130 ± 10 |
| Factor II:C (IU:ml) | 0.1 |
| Factor X:C (IU/ml) | 0.1 |
| Factor VII:C (IU/ml) | 0.1 |
| Factor IXa (%) | 0 |
| AT III (IU/ml) | 0 |

This Factor IX concentrate does not contain any detectable clotting factors (factors XI, XII, prekallikrein HMW kininogen) or any activated factors (thrombin, Xa, pka . . . ). It is also essentially free from other proteins such as inter-alpha-trypsin inhibitor or factor $C_4$ which are major contaminants of the prothrombin complex.

Its thrombogenic activity, as determined by the rabbit statis model (Wessler test), is extremely low: $DE_{50}$>450 IU/kg.

By means of the stabilizers, after resolubilisation, the amount of Factor IX is stable for at least eight hours at room temperature without any loss of activity.

The first human studies do not indicate, at the time of injection, any intolerance reaction. The dosages of Factor V, fibrinogen and blood platelets do not show any variation indicating any possible thrombogenicity of the product.

The injections on human beings indicate a 40 to 49% recovery of Factor IX and a half -life of 20 to 25 hours, thus values comparable to those obtained with PPSB injections.

This concentrate appears as a high-quality product and offers increased safety when treating hemorrhages of B hemophiliacs.

We claim:

1. A method for the separation and purification of a fraction of human plasma for obtaining high-purity Factor IX concentrate for therapeutic use said method consisting essentially of:

(a) forming a supernatant of cryoprecipitated plasma, (b) prepurifying said supernatant of cryoprecipitated plasma by diethylaminoethyl-anion exchange resin chromatography, (c) purifying said prepurified supernatant by a combination of two successive chromatographic steps:
  (i) chromatography on diethylaminoethyl anion exchange resin wherein an ionic force is in the range of 0.34–0.38M sodium chloride, and
  (ii) affinity chromatography of the eluate on heparin-affinity chromatography resin; and (d) recovering said fraction of human plasma containing Factor IX.

2. The method according to claim 1, wherein step (b) is carried out in the presence of heparin.

3. The method according to claim 1, wherein the specific activity of Factor IX in the prepurified fraction is at least 0.5 IU/mg of protein.

4. The method according to claim 3, wherein the specific activity of Factor IX in the prepurified fraction is about 1 IU/mg of protein.

5. The method according to claim 1, wherein a stabilizer for Factor IX is added to the affinity-chromatography elution buffer.

6. The method according to claim 5, wherein the stabilizer is arginine.

7. The method according to claim 6, wherein at least 1 g of arginine is added per liter of buffer.

8. The method according to claim 1, wherein, as a freeze-drying stabilizer, lysine is added to the Factor IX concentrate immediately after it has eluted from the affinity chromatography.

9. The method according to any one of claims 3 to 8, wherein the prepurified fraction is subjected to vital inactivation by solvent-detergent treatment.

10. The method according to claim 1, wherein, after discarding the unadsorbed material flowing through the diethylaminoethyl-anion exchange resin chromatography, elution is performed with a buffer of increasing ionic force in order to separate four fractions enriched respectively in alpha-1-antitrypsin, proconvertin, protein C, protein S and Factor IX.

11. The method according to claim 10, wherein the anion exchange chromatography is preceded by a dilution-filtration step.

12. The method according to claim 1 for obtaining a Factor IX concentrate, wherein the Factor IX is stabilized by adding lysine.

13. The method according to claim 12, wherein the lysine is added before and after separation by affinity chromatography.

14. The method according to claim 1, wherein arginine is added in the elution buffer used for affinity chromatography.

15. A method for the separation and purification of a fraction of human plasma for obtaining high-purity Factor IX concentrate for therapeutic use, said method consisting essentially of:

(a) forming a supernatant of cryoprecipitated plasma;

(b) prepurifying said supernatant of cryoprecipitated plasma by diethyaminoethyl-anion exchange resin chromatography;

(c) purifying the thus obtained prepurified supernatant by chromatography on diethylaminoethyl anion exchange sin with a buffer of increasing ionic force in order to separate four fractions enriched respectively in alpha-1-antitrypsin, proconvertin, protein C, protein S and finally Factor IX, the fraction enriched in Factor IX being obtained by elution with a buffer having an ionic force in the range of 0.34–0.38M sodium chloride at a pH of 7.2 to 7.6;

(d) affinity chromatography of the thus obtained eluate on herapin-affinity chromatography resin; and (e) recovering high-purity Factor IX.

* * * * *